United States Patent [19]

Jautelat

[11] Patent Number: 5,684,203
[45] Date of Patent: Nov. 4, 1997

[54] PROCESS FOR THE PREPARATION OF NITRO-SUBSTITUTED ARYLAMINES

[75] Inventor: Manfred Jautelat, Burscheid, Germany

[73] Assignee: Bayer Aktiengesellschaft, Leverkusen, Germany

[21] Appl. No.: 504,034

[22] Filed: Jul. 26, 1995

[30] Foreign Application Priority Data

Aug. 2, 1994 [DE] Germany .................. 44 27 249.9

[51] Int. Cl.⁶ .................................................. C07C 209/58
[52] U.S. Cl. ........................ 564/406; 564/395; 564/407
[58] Field of Search ..................... 564/395, 406, 564/407

[56] References Cited

U.S. PATENT DOCUMENTS 5,117,063 5/1992 Stern et al. .
5,252,737 10/1993 Stern et al. .................. 544/392

FOREIGN PATENT DOCUMENTS 9324447 12/1993 WIPO .

OTHER PUBLICATIONS

N.R. Ayyanger, et al., Tetrahedron Lett., vol. 31, No. 22, pp. 3217–3220, (1990).

*Primary Examiner*—Brian M. Burn
*Attorney, Agent, or Firm*—Sprung Kramer Schaefer & Briscoe

[57] ABSTRACT

Nitroaromatics can be aminated using urea in the presence of bases and oxygen.

9 Claims, No Drawings

PROCESS FOR THE PREPARATION OF NITRO-SUBSTITUTED ARYLAMINES

The invention relates to a process for the preparation of nitro-substituted arylamines from nitroaromatics, ureas and oxygen in the presence of bases.

Aromatic amines are important intermediates for the production of dyes, crop protection agents, pharmaceuticals and the photographic industry.

Industrially important processes for the preparation of aromatic amines are the reduction of nitro groups in easily accessible nitroaromatics or the reaction of halogenaromatics with ammonia or amines. Although these processes are used industrially on a large scale, unsatisfactory yields often result became of the multi-stage reaction. The direct amination of nitrobenzene using acetanilide in the presence of bases in DMSO is also known, p-nitrosodiphenylamine being formed as main product (Tetrah. Lett. 1990, 22, 3217–3220). In addition, a process is described for the preparation of N-aliphatically substituted p-phenylenediamines by reaction of nitrobenzene with aliphatic amines in the presence of base and proton-containing substances (U.S. Pat. No. 5,252,737). Furthermore, a process is known for the preparation of p-nitroaromatic amides, which describes the reaction of nitrobenzene with amides in the presence of specific bases, such as tetraalkylammonium hydroxides, in the presence of proton-containing substances (WO 93/24447). These processes require special conditions or bases and/or give yields which are not always satisfactory.

Surprisingly, a generally applicable process has now been found for the direct amination of nitro-substituted aromatics using ureas in the presence of simple bases and oxygen. The reactions lead to the corresponding amines in good yields.

The invention relates to a process for the preparation of aromatic amines of the formula

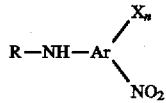
(I)

in which

Ar denotes a monocyclic or polycyclic, preferably monocyclic or bicyclic, aromatic radical having 4 to 16 C atoms, which can also contain 1 to 2 heteroatoms selected from the group consisting of N, O and S, R denotes hydrogen, $C_1$–$C_8$-alkyl, $C_2$–$C_8$-alkenyl, $C_3$–$C_7$-cycloalkyl, $C_6$–$C_{14}$-aryl, where these substituents can be monosubstituted to trisubstituted by halogen, $C_1$–$C_4$-alkyl, amino and/or $C_1$–$C_4$-alkoxy, X denotes halogen, cyano, $C_1$–$C_4$-alkyl, halogenated $C_1$–$C_4$-alkyl, $C_1$–$C_4$-alkoxy, halogenated $C_1$–$C_4$-alkoxy, $C_1$–$C_4$-alkylmercapto, halogenated $C_1$–$C_4$-alkylmercapto, $C_1$–$C_4$-alkylsulfonyl or nitro, n denotes zero, 1, 2 or 3, preferably zero, 1 or 2, where for n>1 the substituent X can be different, by which nitroaromatics of the formula

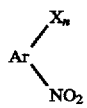
(II)

in which

X, Ar and n have the meanings given above, are reacted with ureas of the formula

(III)

in which the two substituents R are identical or different and have the meaning given above and Y represents O or S, in the presence of bases together with oxygen in polar solvents.

Preferred aromatic $C_4$–$C_{16}$ radicals include for example benzene, naphthalene, pyridine, quinoline and thiophene radicals, preferably benzene and naphthalene radicals.

"$C_1$–$C_8$-alkyl" and "$C_1$–$C_4$-alkyl" include linear and branched radicals such as methyl, ethyl, isopropyl and n-, sec- and tert-butyl.

"$C_2$–$C_8$-alkenyl" includes vinyl and allyl.

"$C_3$–$C_7$-cycloalkyl" includes cyclopropyl, cyclopentyl and cyclohexyl.

"$C_6$–$C_{14}$-aryl" represents unsubstituted or substituted aryl radicals such as phenyl or naphthyl each of which may be monosubstituted or polysubstituted by halogen, alkyl, nitro, amino, alkoxy, alkylthio, sulphonic acid, hydroxyl, formyl, benzoyl, carboxyl, cyano, phenyl and phenylalkyl.

"Halogen" represents bromine, iodine, preferably fluorine and chlorine.

"Halogenated $C_1$–$C_4$-alkyl" includes e.g. trifluoromethyl and dichlorofluoromethyl.

"$C_1$–$C_4$-alkoxy" preferably denotes methoxy, "halogenated $C_1$–$C_4$-alkoxy", preferably represents trifluoromethoxy.

"$C_1$–$C_4$-alkylmercapto" preferably denotes methylmercapto; "halogenated $C_1$–$C_4$-alkylmercapto" preferably represents trifluoromethylmercapto.

"$C_1$–$C_4$-alkylsulphonyl" preferably represents methylsulphonyl.

Preferred nitroaromatics (II) include, for example, nitrobenzene, m-chloronitrobenzene, m-nitrobenzonitrile, m-trifluoromethylnitrobenzene, 3-fluoro-nitrobenzene, 3-nitrotoluene, 3-trifluoromethoxynitrobenzene, 3-trifluoromethylthio-nitrobenzene, 3,5-dichloronitrobenzene, 2-nitrobenzonitrile, 2-nitrobenzoic acid, 1-nitronaphthalene, 2-nitronaphthalene, 2-nitrothiophene, 3-nitrothiophene, 2-nitrofuran, N-alkylated and N-arylated 2- and 3-nitropyrrols, 2-, 3- and 4-nitro-pyridine, 4-ethoxy-3-nitropyridine, 5-, 6- and 8-nitroquinoline.

Preferred ureas of the formula (III) include, for example, urea, thiourea, methylurea, N,N'-dimethylurea, N,N'-diethylurea, N,N'-dibutylthiourea, phenylurea, N,N'-diphenylurea, N,N'-diisopropylthiourea, allylthiourea, N,N'-di-p-tolylthiourea, N,N'-di-(4-chlorophenyl)-urea.

Particular preference is given to the symmetrically substituted ureas of the formula (III).

Suitable bases are either organic or inorganic bases; preference is given to inorganic bases, such as alkali metal hydroxides, alkali metal amides, alkali metal alkoxides or alkali metal hydrides. Particular preference is given to alkali metal hydroxides, such as lithium hydroxide, sodium hydroxide, potassium hydroxide, caesium hydroxide, potassium tert-butoxide. The bases are preferably used in the form of powders or microgranules (micropills).

Oxygen can be used as pure gas or particularly preferably in mixtures with other gases, for example in the form of air.

Suitable solvents for the preparation of the compounds (I) according to the invention include organic or inorganic solvents. Preferred organic solvents are polar aprotic solvents, such as dimethyl sulphoxide, dimethylformamide, N-methylpyrrolidone, pyridine, dioxane, THF, acetonitrile, sulpholane and mixtures thereof. A preferred inorganic solvent is, for example, liquid ammonia. Small amounts, i.e. up to 10% by weight, based on total solvent, of proton-containing solvents, such as water for example, are acceptable. The preferred solvent is dimethyl sulphoxide.

The reaction can be carried out within a broad temperature range. Temperatures between −35° C. and 120° C. are generally employed, preferably between 20° C. and 80° C.

When the process according to the invention is carried out, atmospheric pressure is generally employed; however it is also possible to employ elevated or reduced pressure.

When the process according to the invention is carried out, per mol of the nitroaromatic of the formula (II), generally 0.5 to 10 mol, preferably 0.7 to 2 mol, of ureas of the formula (III) are used and 1 to 10 equivalents, preferably 2 to 6 equivalents, of base. Oxygen is preferably introduced in excess undiluted or diluted.

If 3-nitrobenzotrifluoride, N,N'-diphenylurea and air are used as starting materials and sodium hydroxide is used as base, the course of the process for the preparation of nitro-substituted amines can be expressed by the following formula diagram:

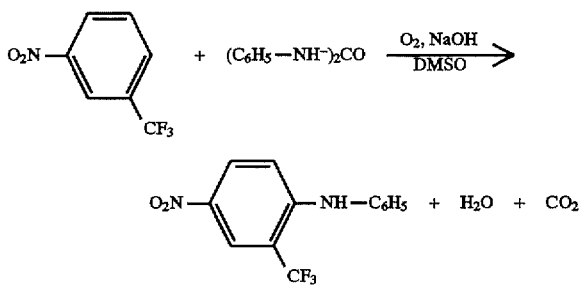

The starting materials of the formulae (II) and (III) are known or can be prepared by known processes.

The work-up can be performed by the usual methods. In general, the procedure is performed so that the reaction mixture is greatly diluted with water and the reaction product precipitating is separated off and isolated, or the mixture is diluted with water and extracted with an organic solvent sparingly miscible with water. The product is isolated from the organic phase after this has been dried and concentrated.

EXAMPLES

Example 1

N-methyl-4-nitro-2-trifluoromethylaniline 1.91 g (10 mmol) of 3-nitrobenzotrifluoride and 1.76 g (20 mmol) of N,N'-dimethylurea are heated to 50° C. for 4 h with 1.2 g (30 mmol) of sodium hydroxide in the form of microbeads in 30 ml of DMSO, passing through an airstream. The mixture is then diluted with ethyl acetate and washed repeatedly by shaking with sainted soda solution. After drying the organic phase over sodium sulphate and taking off the solvent, 2.2 g (10 mmol, 100%) of N-methyl-4-nitro-2-trifluoromethylaniline are obtained as a 95% pure product of m.p. 99°–101° C. After recrystallization from ethanol the product has a m.p. of 111°–112° C.

Example 2

N-butyl-4-nitro-2-trifluoromethylaniline 1.91 g (10 mmol) of 3-nitrobenzotrifluoride and 3.76 g (20 mmol) of N,N'-dibutylthiourea are heated to 50° C. for 6 h with 1.2 g (30 mmol) of NaOH micropills in 30 ml of absolute DMSO, passing through dry air. Work-up ming ethyl acetate and soda solution leads to 5.6 g of crude product which is purified by chromatography using petroleum ether/ethyl acetate (1:1 parts by volume) on silica gel: 2.1 g (8 mmol, 80%) of N-butyl-4-nitro-2-trifluoromethylaniline as oil. $^1$H-NMR (CDCl$_3$, 200 MHz): δ1.0 (t, 3H), 1.5 (m, 2H), 1.7 (m, 2H), 3.3 (m, 2H), 5.05 (s, NH), 6.75 (d, 1H), 8.25 (dd, 1H), 8.4 (d, 1H)

Example 3

4-Nitrodiphenylamine 1.23 g (10 mmol) of nitrobenzene, 2.12 g (10 mmol) of N,N'-diphenylurea and 1.2 g (30 mmol) of NaOH micropills are heated to 50° C. for 23 h in 30 ml of absolute DMSO, passing through an airstream. After work-up using ethyl acetate and soda solution, 2.0 g (9.3 mmol, 93%) of product are obtained which melts at 128° C. after recrystallization from cyclohexane.

The following compounds are prepared in accordance with Examples 1 to 3:

| No. | Product | m.p. |
|---|---|---|
| 4 | O$_2$N—C$_6$H$_3$(CF$_3$)—NH—Ph | 59–60° C. |
| 5 | O$_2$N—C$_6$H$_3$(CF$_3$)—NH$_2$ | 89–91° C. |

I claim:

1. A process for the preparation of a compound of the formula $$R-NH-Ar\begin{matrix}X_n\\ \\NO_2\end{matrix} \qquad (I)$$

in which

Ar denotes a monocyclic or polycyclic, aromatic C$_4$–C$_{16}$ radical, which can also contain 1 to 2 heteroatoms selected from the group consisting of N, O and S, R denotes hydrogen, C$_1$–C$_8$-alkyl, C$_2$–C$_8$-alkenyl, C$_3$–C$_7$-cycloalkyl and C$_6$–C$_{14}$-aryl, where these substituents are optionally monosubstituted to trisubstituted by halogenated, C$_1$–C$_4$-alkyl, amino and/or C$_1$–C$_4$-alkoxy, X denotes halogen, cyano, C$_1$–C$_4$-alkyl, halogenated C$_1$–C$_4$-alkyl, C$_1$–C$_4$-alkoxy, halogenated C$_1$–C$_4$-alkoxy, C$_1$–C$_4$-alkylmercapto, halogenated C$_1$–C$_4$-alkylmercapto, C$_1$–C$_4$-alkylsulfonyl or nitro, n denotes zero, 1, 2 or 3 where for n>1 the substituents X can be different, which comprises reacting a nitroaromatic compound of the formula

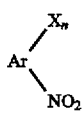 (II)

in which
X, Ar and n have the meanings given above, with a urea of the formula

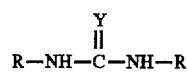 (III)

in which the two substituents R are identical or different and have the meaning given above and Y represents oxygen or sulfur in the presence of an inorganic or organic base and oxygen, in a polar solvent wherein 0.5 to 10 mol of the urea of formula (III) is used per mol of the nitroaromatic of formula (II) and 1 to 10 equivalents of base are present and at a temperature between $-35°$ C. and $120°$ C.

2. The process according to claim 1, wherein

Ar denotes a monocyclic or bicyclic, aromatic $C_4$–$C_{10}$ radical, which can also contain 1 to 2 heteroatoms selected from the group consisting of N, O and S, R denotes hydrogen, $C_1$–$C_4$-alkyl, $C_2$–$C_3$-alkenyl, $C_3$–$C_6$-cycloalkyl and $C_6$–$C_{10}$-aryl, where these substituents can be monosubstituted to trisubstituted by halogen, $C_1$–$C_4$-alkyl, amino and/or $C_1$–$C_4$-alkoxy, X denotes halogen, cyano, $C_1$–$C_4$-alkyl, halogenated $C_1$–$C_4$-alkyl, $C_1$–$C_4$-alkoxy, halogenated $C_1$–$C_4$-alkoxy, $C_1$–$C_4$-alkylmercapto, halogenated $C_1$–$C_4$-alkylmercapto, $C_1$–$C_4$-alkylsulfonyl or nitro, n denotes zero, 1, 2 or 3 where for n>1 the substituents X can be different.

3. The process according to claim 1 wherein

Ar denotes benzene, naphthalene, pyridine, quinoline, thiophene, furan, and pyrrol, R denotes hydrogen, $C_1$–$C_8$-alkyl, $C_2$–$C_8$-alkenyl, $C_3$–$C_7$-cycloalkyl and $C_6$–$C_{14}$-aryl, where these substituents are optionally monosubstituted to trisubstituted by halogen, $C_1$–$C_4$-alkyl, amino and/or $C_1$–$C_4$-alkoxy, X denotes halogen, cyano, $C_1$–$C_4$-alkyl, halogenated $C_1$–$C_4$-alkyl, $C_1$–$C_4$-alkoxy, halogenated $C_1$–$C_4$-alkoxy, $C_1$–$C_4$-alkylmercapto, halogenated $C_1$–$C_4$-alkylmercapto, $C_1$–$C_4$-alkylsulfonyl or nitro, n denotes zero, 1, 2 or 3 where for n>1 the substituents X can be different.

4. The process according to claim 1, wherein

Ar denotes benzene, naphthalene, pyridine, quinoline and thiophene.

5. The process according to claim 1, wherein the temperature is between $20°$ C. and $80°$ C.

6. The process according to claim 1, wherein the base is an alkali metal hydroxide, an alkali metal amide, an alkali metal alkoxide or an alkali metal hydride.

7. The process according to claim 1, wherein the solvent is a polar aprotic solvent.

8. The process according to claim 1, wherein the base is NaOH and the solvent is DMSO.

9. The process according to claim 1, wherein 0.7 to 2 mol of the urea of formula III per mol of the nitroaromatic of formula III is used.

* * * * *